(12) United States Patent
Hamano et al.

(10) Patent No.: US 7,896,006 B2
(45) Date of Patent: Mar. 1, 2011

(54) MEDICINE INHALER AND MEDICINE EJECTION METHOD

(75) Inventors: Soji Hamano, Yokohama (JP); Mitsuru Imai, Chichibu (JP)

(73) Assignee: Canon Kabushiki Kaisha, Tokyo (JP)

( * ) Notice: Subject to any disclaimer, the term of this patent is extended or adjusted under 35 U.S.C. 154(b) by 900 days.

(21) Appl. No.: 11/776,872

(22) Filed: Jul. 12, 2007

(65) Prior Publication Data

US 2008/0022998 A1    Jan. 31, 2008

(30) Foreign Application Priority Data

Jul. 25, 2006 (JP) .............................. 2006-201432
Jul. 5, 2007 (JP) .............................. 2007-177023

(51) Int. Cl.
*A61M 11/00* (2006.01)

(52) U.S. Cl. ............................ 128/204.15; 128/204.29; 128/204.22; 128/204.21

(58) Field of Classification Search ............ 128/204.15, 128/204.18, 204.21, 204.22, 204.29
See application file for complete search history.

(56) References Cited

U.S. PATENT DOCUMENTS

| 7,461,655 | B2 * | 12/2008 | Sexton et al. | 128/204.15 |
| 2003/0101991 | A1 * | 6/2003 | Trueba | 128/200.14 |
| 2006/0162723 | A1 | 7/2006 | Selzer et al. | 128/200.14 |
| 2007/0062520 | A1 | 3/2007 | Nobutani et al. | 128/200.14 |
| 2007/0227534 | A1 | 10/2007 | Nobutani et al. | 128/200.14 |
| 2007/0240706 | A1 | 10/2007 | Kobayashi et al. | 128/200.14 |
| 2007/0240711 | A1 | 10/2007 | Hamano | 128/203.12 |
| 2008/0011292 | A1 | 1/2008 | Sugita et al. | 128/200.19 |
| 2008/0163869 | A1 | 7/2008 | Nobutani et al. | 128/200.23 |

FOREIGN PATENT DOCUMENTS

| EP | 1452199 | 9/2004 |
| WO | 95/01137 A1 | 1/1995 |
| WO | WO 95/01137 | 1/1995 |
| WO | WO 98/48873 | 11/1998 |
| WO | WO 00/05011 | 8/2000 |
| WO | 02/04043 A2 | 1/2002 |
| WO | WO 2004/004813 | 1/2004 |
| WO | 2006/013952 A1 | 2/2006 |
| WO | WO 2007/011866 | 1/2007 |

* cited by examiner

*Primary Examiner*—Steven O Douglas
(74) *Attorney, Agent, or Firm*—Fitzpatrick, Cella, Harper & Scinto

(57) ABSTRACT

A medicine ejection device is provided allowing a medicine with a desired droplet diameter to be inhaled at a constant rate. The medicine ejection device has a decision part at which the ejection operating conditions of a medicine ejection part for ejecting the medicine are decided in accordance with at least one of an open-air environment or a state of the medicine during use of the device. The device ejects the medicine according to the ejection operating conditions decided by the decision part.

4 Claims, 8 Drawing Sheets

MEDICINE INHALER AND MEDICINE EJECTION METHOD

BACKGROUND OF THE INVENTION

1. Field of the Invention

This invention relates to a medicine ejection device such as an inhaler, which ejects medicines to be administered to users.

2. Related Background Art

In medicine inhalers which allow users to inhale and take medicines, treatment for users is being realized in which information databases such as electronic medical records can be utilized. Such medicine inhalers are portable terminals having in combination i) a memory means which stores information concerned with each individual user, inclusive of information on user's medical records and prescription and ii) a medicine ejection device which ejects a medicine to allow users to inhale it. They also have an ejection control means which controls the medicine ejection device in accordance with inspiration profiles of users to eject the medicine so that the users can inhale the medicine in conformity with prescription information.

In the medicine inhalers described above, a method is employed in which proper liquid droplets are ejected in a predetermined number from an ejection head (through an ejection orifice) by a system in which a liquid is ejected by producing air bubbles with a heater in the open air, i.e., air streams, to be inhaled by a user through a suction port, or a system in which a liquid is ejected by the aid of mechanical energy of a piezoelectric element.

The above conventional medicine ejection device has a problem in that the quantity of a medicine capable of being inhaled may greatly change depending on open-air environmental conditions (such as temperature, humidity and atmospheric pressure) during use of the device and on the condition of the medicine.

First, in the case of a liquid medicine, viscosity increases as the temperature of the liquid drops, and hence the volume of ejection liquid droplets tends to decrease. In particular, in the system in which the liquid is ejected by producing air bubbles with a heater, if the liquid comes to have a low temperature, thus has a high viscosity, the volume of bubbles to be produced may become small or it becomes difficult to generate bubbles. This brings about a decrease in the total amount of liquid droplets to be ejected from an ejection head, even if electric pulses are repeatedly supplied for a certain time to an electrothermal conversion element serving as a heater. As a result, the user may inhale the medicine in a smaller quantity.

If the open air comes to have a low temperature, it inevitably affects the medicine temperature. Also, as a factor other than that, it takes a time to raise the temperature of an ejection head at the initial stage of an ejection operating period of the ejection head, and hence the head comes to have poor ejection performance especially at the initial stage of the ejection operating period, resulting in a decrease in the total amount of liquid droplets to be ejected.

Depending on the humidity of the air to be sucked, the diameters of liquid droplets are changed after they have been ejected because the liquid droplets ejected from an ejection head are very small. Commonly, in order to enable intracorporeal absorption through lung alveoli, it is physiologically desirable that the liquid droplets have a diameter of about 3 µm. For example, where the medicine is ejected setting the ejection head to have a nozzle diameter of 3 µm, many liquid droplets can maintain a droplet diameter of 3 µm as long as the air is kept at a humidity as high as about 90%. However, the medicine may become deposited on the target administration portion in a smaller quantity because liquid droplets increase which come to have a smaller diameter with a decrease in humidity. In this connection, if the liquid droplets come to have too small a diameter, they are inevitably extracorporeally discharged with the user's exhaled air. As a result, the user can not inhale the medicine in a desired quantity.

The medicine comes to have a lower boiling point with a decrease in atmospheric pressure. Hence, the quantity of the medicine to be ejected tends to increase.

It is essential that the medicine be refrigerated so as not to lose its efficacy. In some cases, it is desirable that the medicine is inhaled immediately after it has been taken out of a refrigerator. For example, there may be even a case in which, while the open-air temperature at the time of inhalation is 25° C., the medicine temperature is 5° C. When the medicine inhaler is carried outdoors, there may also be a case in which the medicine is kept at a temperature close to body temperature (e.g., when carried on the body) and the inhaler is in a cold environment of about 10° C. In such a cold environment, the medicine temperature may be higher than the open-air temperature. Thus, there are circumstances where use conditions are so varied that it is difficult to make the dose of medicine constant.

SUMMARY OF THE INVENTION

An object of the present invention is to provide a medicine ejection device which can make the dose of medicine more accurate to enable a medicine to be efficiently inhaled, under any fluctuations of environmental conditions upon inhalation of the medicine. That is, the present invention provides a medicine ejection device for allowing a medicine with a desired droplet diameter to be inhaled at a constant rate.

To achieve the above object, the medicine ejection device according to the present invention, which ejects a medicine to be administered to a user, has the following: a decision part at which ejection operating conditions of a medicine ejection part for ejecting the medicine are decided in accordance with at least one of an open-air environment and a state of the medicine during use of the device; the device ejecting the medicine according to the ejection operating conditions decided by the decision part.

The medicine ejection device of the present invention is constituted as described above, and hence brings about such effects as stated below.

Fluctuations of the quantity of the liquid medicine to be ejected or fluctuations of the total amount of the liquid medicine having been ejected and having the desired droplet diameter, which are caused by changes in an open-air environment during use of the device or changes in the state of the medicine, are corrected to enable the user to inhale the medicine in an accurate dose conforming to prescription. As a result, any mental and physical load can be lessened and the medicine can surely be sent to the lungs in an effective dose to enable the medicine to be effectively administered.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Preferred embodiments of the present invention will be described in detail with reference to the accompanying drawings.

The medicine ejection device of the present invention is characterized by having a decision part at which the operating conditions of a medicine ejection part for ejecting a medicine are decided in accordance with an open-air environment during use of the device or the state of the medicine. This decision part exists in a control part (a controller) of the medicine ejection device, and sends drive signals to the medicine ejection part (an ejection head) according to the ejection operating conditions decided by the decision part. The medicine ejection part ejects a medicine in accordance with drive signals. This enables liquid droplets with a desired droplet diameter to be inhaled at a constant rate without regard to any environmental changes during use of the device and any changes in the state of the medicine.

Desirable parameters to be taken into account in order to decide the ejection operating conditions may include open-air temperature, open-air humidity and open-air atmospheric pressure. Any changes in these cause fluctuations in the quantity of the liquid medicine to be ejected, the total amount of the liquid medicine to be ejected or the total amount of the liquid medicine having been ejected and having the desired droplet diameter. Also, the state of medicine that should be taken into account may include medicine temperature and medicine viscosity. Any changes in these cause fluctuations in the above respective total amounts, i.e., the ejection quantity of the medicine. The medicine ejection device of the present invention compensates such fluctuations, and decides the ejection operating conditions of the medicine ejection part ejecting the medicine on the basis of at least one value of the above parameters so that a user can inhale the medicine in a constant dose.

A method which allows the medicine ejection device to recognize actual measurements of the above parameters may be arbitrarily employed. As one feasible embodiment, it is conceivable that a user inputs measured values of open-air temperature, open-air humidity and so forth before use. In this case, it follows that the medicine ejection device has an input button with which the user inputs the measured values and the decision part decides the ejection operating conditions on the basis of the values inputted.

As another embodiment, it is also preferable that the medicine ejection device itself has at least one of a medicine temperature measuring sensor which measures the temperature of the medicine, a temperature sensor which measures the temperature of open air, a humidity sensor which measures the humidity of open air and an atmospheric-pressure sensor which measures the atmospheric pressure of open air. In this case, the decision part decides the ejection operating conditions of the medicine ejection part for ejecting the medicine, on the basis of a measured value found by selecting at least one of these sensors. Setting up in this way can save the user from making an input and enables the device to automatically decide appropriate ejection operating conditions. Hence, this is more user-friendly.

In the present invention, the medicine ejection part (ejection head) may have any desired ejection pressure generation element. It may be exemplified by an electrothermal conversion element which provides the medicine with thermal energy or an electromechanical conversion element which provides the medicine with mechanical energy. That is, a method for ejecting the medicine may be exemplified by a method in which the electrothermal conversion element is used to provide the medicine with thermal energy to eject it (a thermal jet system), and a method in which vibratory pressure of an electromechanical conversion element (e.g., a piezoelectric element) which provides the medicine with mechanical energy is used to eject the medicine. An ejection method may be selected in accordance with, e.g., the type of medicine.

When the thermal jet system is used, it is possible to enhance the size precision and reproducibility of, for example, the orifice diameter of the ejection orifice, calorie of heat pulses utilized for ejection and a micro-heater as the electrothermal conversion element in respect of individual liquid ejection units. Hence, a narrow droplet diameter distribution can be achieved. In addition, production cost for the head can be so low that this system is highly adaptable to compact devices which require frequent replacement of heads. Accordingly, the medicine ejection device of such a thermal jet system is particularly preferred when the medicine ejection device is required to have portability and convenience.

Methods of deciding ejection operating conditions for allowing the user to inhale at a constant rate the liquid droplets with the desired droplet diameter may include the following.

First, a method may be conceived in which an ejection operating period is decided for which the medicine is to be ejected in a quantity corresponding to the dose of the medicine. The “ejection operating period” herein termed refers to a length of time passing after the ejection pressure generation element has been provided with the first pulse and until it has been provided with the last pulse. That is, it refers to a period of time for which a series of pulses for generating ejection energy are supplied. Making the ejection operating period longer can make medicine ejection quantity larger. Even without changing the ejection operating period, the ejection quantity can also be changed by changing the ejection frequency of the ejection pressure generation element. Here, the “ejection frequency” corresponds to the number of pulse signals for ejecting the medicine which are applied to the ejection pressure generation element per unit time. The quantity of the medicine to be ejected can also be changed by changing pulse width. The "pulse width" is an electrification time for applying pulse signals once. Elongating the pulse width increases the quantity of the medicine to be ejected in accordance with the pulse signals applied once.

These methods may be used in combination to change the medicine ejection quantity for achieving the necessary dose. In short, it suffices as long as the amount of energy applied to the medicine can be controlled, and any method may be used therefor. Since, however, individual devices have functional restrictions on drive frequencies, it is simple to use a controlling method to conduct changes in the ejection operating period.

The medicine usable in the present invention includes not only medicines including pharmaceutical compounds capable of exhibiting pharmacological and physiological actions, but also flavoring components, dyes, pigments, etc. The medicine may be liquid or powdery.

The liquid medicine used in the present invention refers to a medicine in the form of a liquid or a liquid medium containing a medicine. The liquid medicine may contain any desired additive(s). The medicine in a liquid may be in the state of any of dissolution, dispersion, emulsification, suspension and slurry, and is preferably homogenized in the liquid.

In the case where the liquid medicine is used as the medicine, the primary medium of the liquid is preferably water or organic matter. Taking into account the fact that the medicine is administered to living bodies, it is preferable that the chief medium is water.

The medicine ejection device according to the present invention is described below in greater detail by way of examples in which it is used as an inhaler.

EXAMPLE 1

Figure 1:
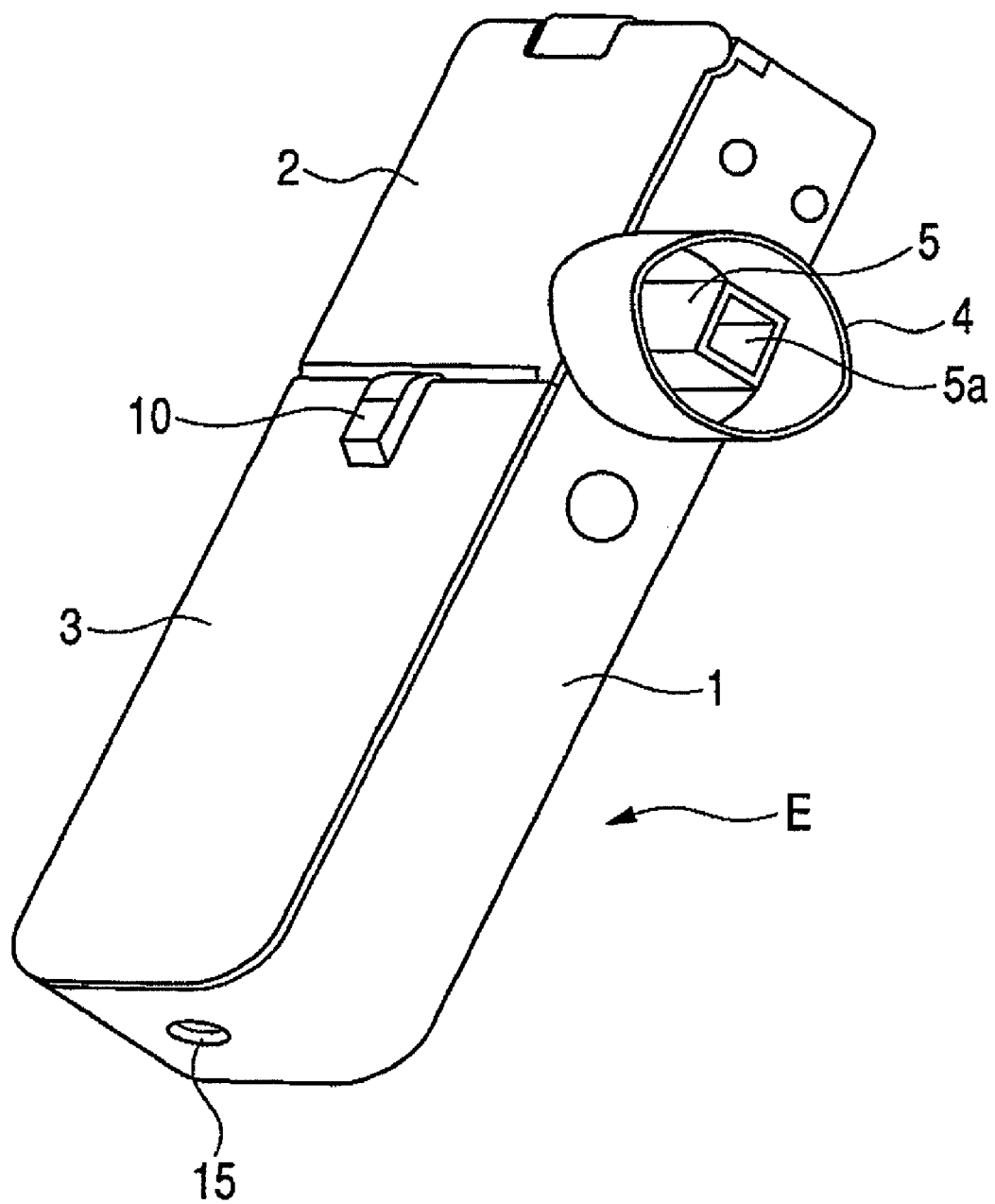
FIG. 1 is a perspective view showing an example of an inhaler according to an embodiment of the medicine ejection device of the present invention.
Figure 2:
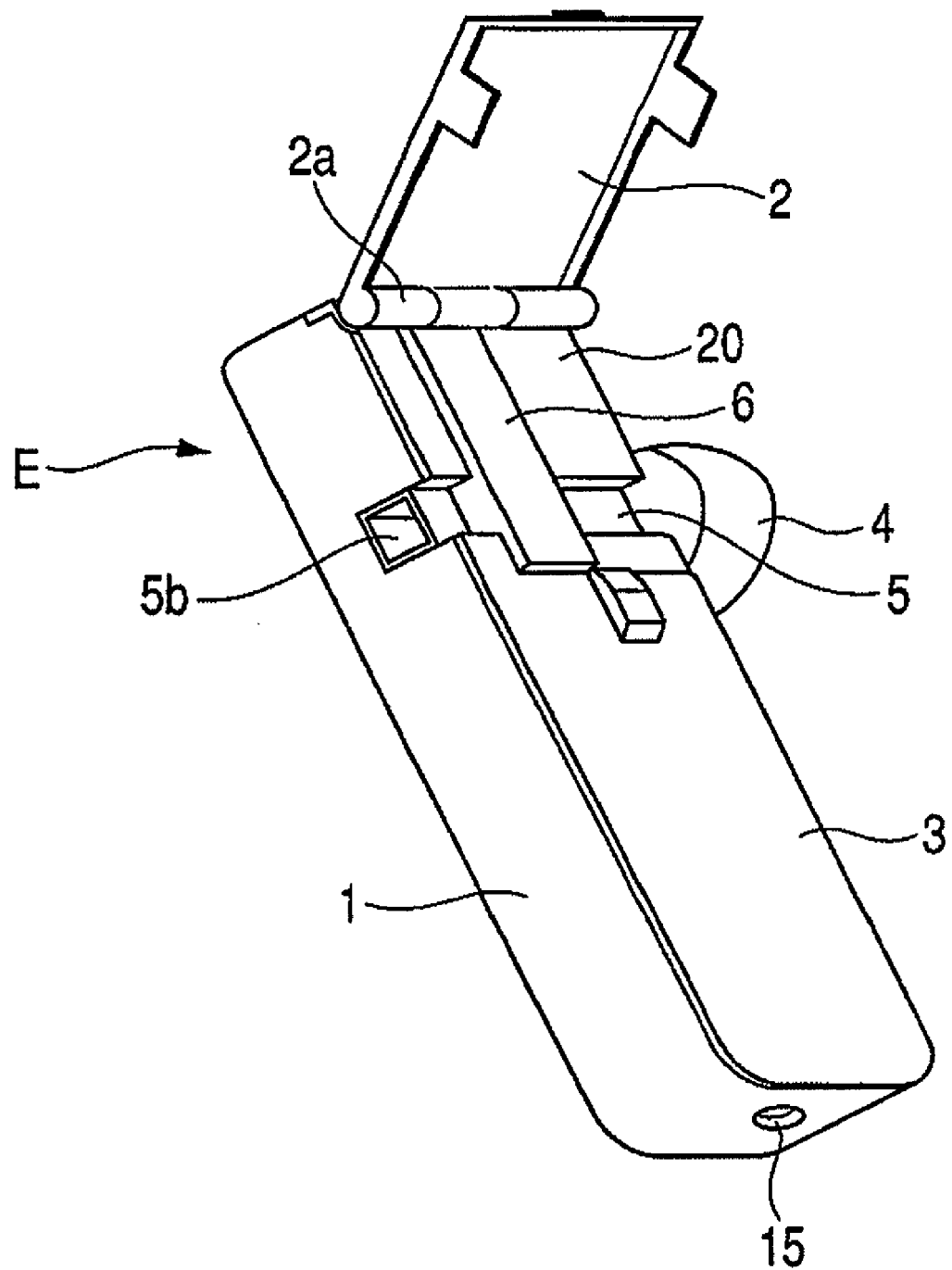
FIG. 2 is a perspective view showing a state in which an access cover of the inhaler shown in FIG. 1 is opened.

FIG. 1 is a perspective view showing the appearance of an inhaler according to an embodiment of the medicine ejection device of the present invention. In FIG. 1, reference character 5a denotes an outlet. FIG. 2 is a perspective view showing a state in which an access cover of the inhaler shown in FIG. 1 is opened. In FIG. 2, reference character 2a denotes a hinge and reference character 5b denotes an intake (inlet).

An inhaler E of this Example includes a box-like housing main body 1, and a front cover 3 and an access cover 2 provided on its openable side.

The front cover 3 is integrally provided so as to close the openable side of the housing main body 1 at the one-side top in the lengthwise direction. The access cover 2 is swing-movably fitted via a hinge 2a, to the other end of the openable side of the housing main body 1 in the lengthwise direction, and is always pressed by a return spring (not shown) in the opening direction. The front cover 3 is provided with a lock lever 10 having a projection 10a (FIG. 4A) engaged with an end (free end) of the access cover 2, in order for the access cover 2 not to be opened carelessly.

The lock lever 10 can be slid against elastic force of the return spring, whereupon the projection 10a comes out of the end of the access cover 2, and the access cover 2 swing-moves around a hinge shaft (not shown) by the aid of the return spring to be opened.

As shown in FIG. 2, as the access cover 2 is opened, a medicine ejection unit 6 integrally holding an ejection head 8 and a medicine tank (medicine holder) 7 (FIG. 3) and a flow path 5 connected with a mouthpiece 4 come to appear. The medicine ejection unit 6 and the mouthpiece 4 are detachably supported on a guide 20 of the housing main body 1.

Figure 3:
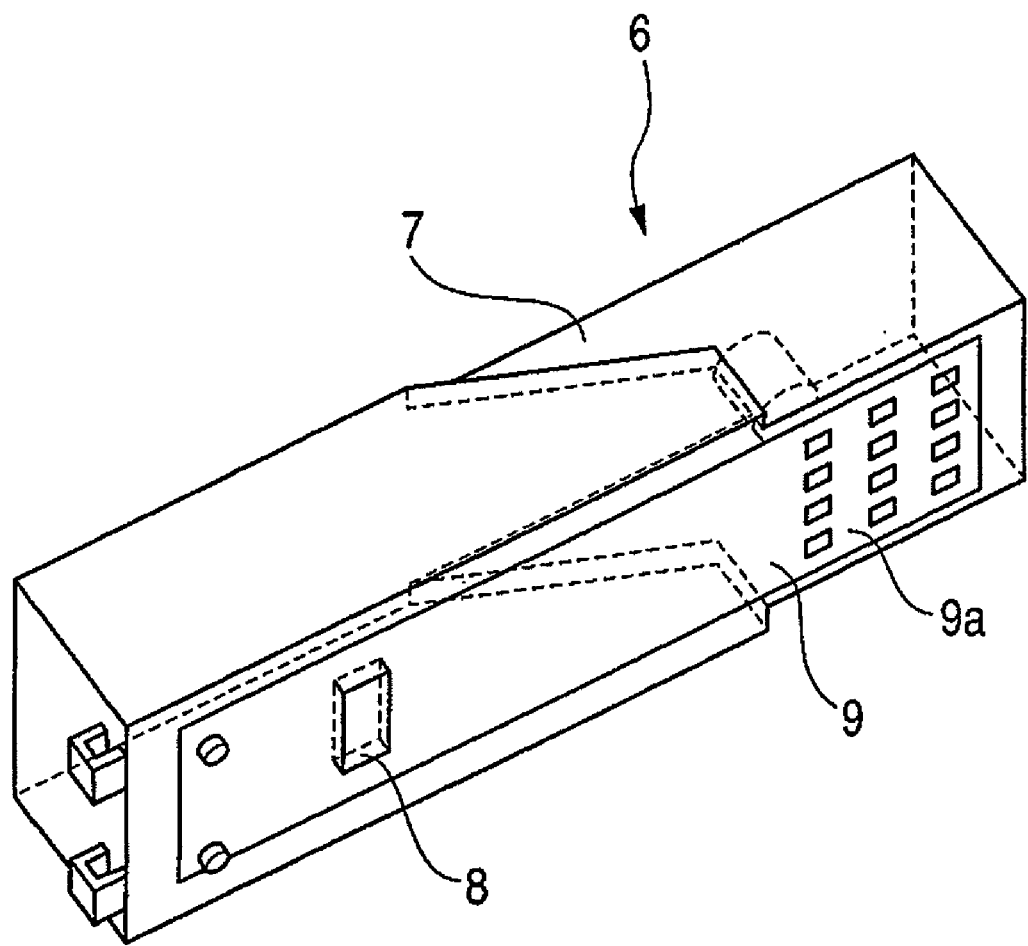
FIG. 3 is a perspective view of a medicine ejection unit in the inhaler shown in FIG. 1.

As shown in FIG. 3, the medicine ejection unit 6 consists basically of the medicine tank 7 which holds the medicine therein, the ejection head 8 which ejects the medicine therefrom, and a member 9 having an electrical connection surface 9a connected with a battery 18 (FIG. 4) which supplies electric powder to a heater (not shown) provided on the ejection head 8 to generate heat energy. Rechargeable secondary cells are used in the battery 18. The medicine tank and the ejection head may be integrally formed into a cartridge in this way, or the medicine tank and the ejection head may be individually set up as separate members.

Figure 4A:
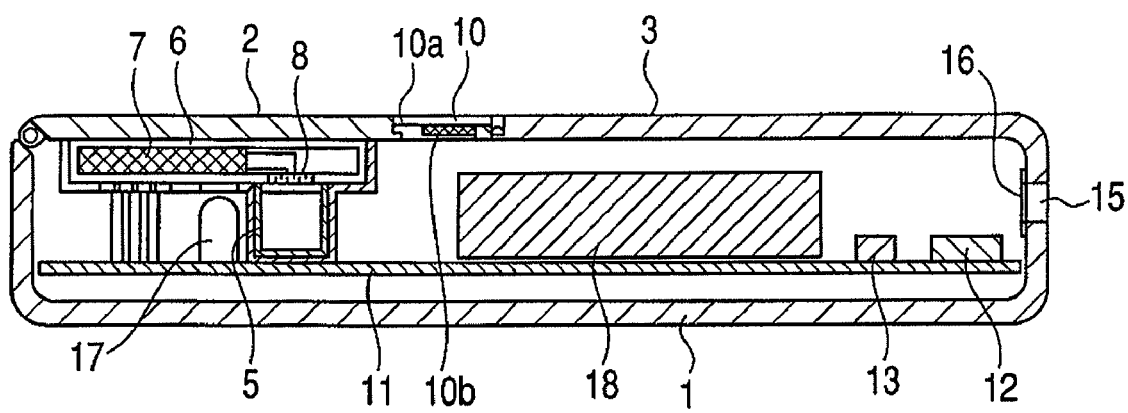
FIG. 4A is a vertical section of the inhaler shown in FIG. 1.
Figure 4B:
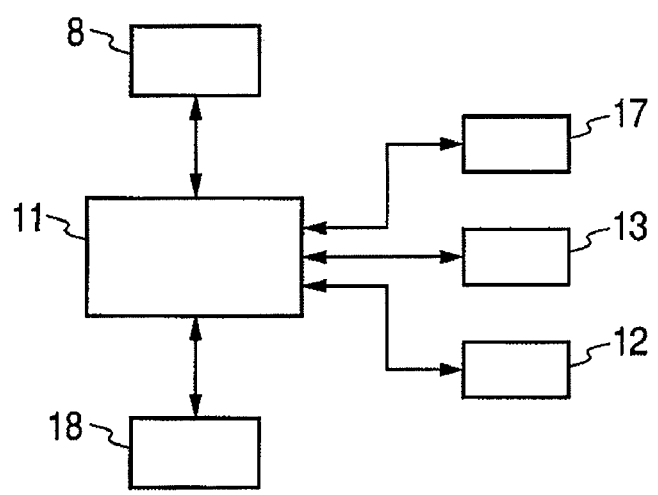
FIG. 4B is an electrical block diagram of the inhaler shown in FIG. 4A.

FIG. 4A is a vertical section of the inhaler shown in FIG. 1. FIG. 4B is an electrical block diagram of the inhaler. In the following, a case is described in which the decision part regulates the ejection operating period under such a constitution that the inhaler itself has a means for examining the open-air environment and the state of the medicine.

A temperature-humidity sensor 12 which measures temperature and humidity of the open air and a pressure sensor 13 for measuring open-air atmospheric pressure are provided on a control motherboard 11. The control motherboard 11 (a control part) is also provided therein with, though not shown in the drawings, i) a decision part which decides the ejection operating period for which the liquid droplets are to be ejected in a quantity corresponding to the dose of the medicine and ii) a control means for outputting orders to perform ejection according to the ejection operating period thus decided; where the medicine ejection quantity of the inhaler E at the time of inhalation conforms to prescription. More specifically, it is provided with a ROM in which a control program is stored and a RAM in which a data table showing the relationship between the above respective measured values and their correction factors is stored, on the basis of which data table the ejection operating period is decided. In addition to these, it is provided with at least a CPU which reads the data of the above ROM or RAM and performs arithmetic operation to decide the ejection operating period and control the ejection unit 6.

The open-air environmental conditions (temperature, humidity and atmospheric pressure) are measured which has been sucked into the housing through an open-air communicating aperture 15 made in the housing main body 1. It is preferable that the communicating aperture 15 is provided on the inside of the housing with a shielding sheet 16 made of a material having a fine continuous porous structure which prevents water from entering, but passes air. This is to provide the device with waterproofness to improve safety required as electrical equipment, because the medicine is a liquid and the mouthpiece 4 must be washed unless it is disposable.

A temperature sensor 17 of the medicine tank 7 is also provided on the control motherboard 11 to measure the surface temperature of the medicine tank 7. It is best if the temperature of the medicine is directly measured. However, since the medicine is held in a closed container so that any sundry germs may not mix in the medicine, it is difficult to directly measure the temperature. Accordingly, the surface temperature of the medicine tank 7 is measured as being substantially equal to the medicine temperature, and is substituted for the medicine temperature.

The measured values of the open-air temperature and open-air humidity measured with the temperature-humidity sensor 12, the measured value of the open-air atmospheric pressure measured with the pressure sensor 13 and the measured value of the medicine temperature measured with the temperature sensor 17 are transmitted to the control part 11, and the ejection operating period is decided at the control part 11. The control part 11 sends drive signals to the ejection head 8 (FIG. 4B).

Figure 5:
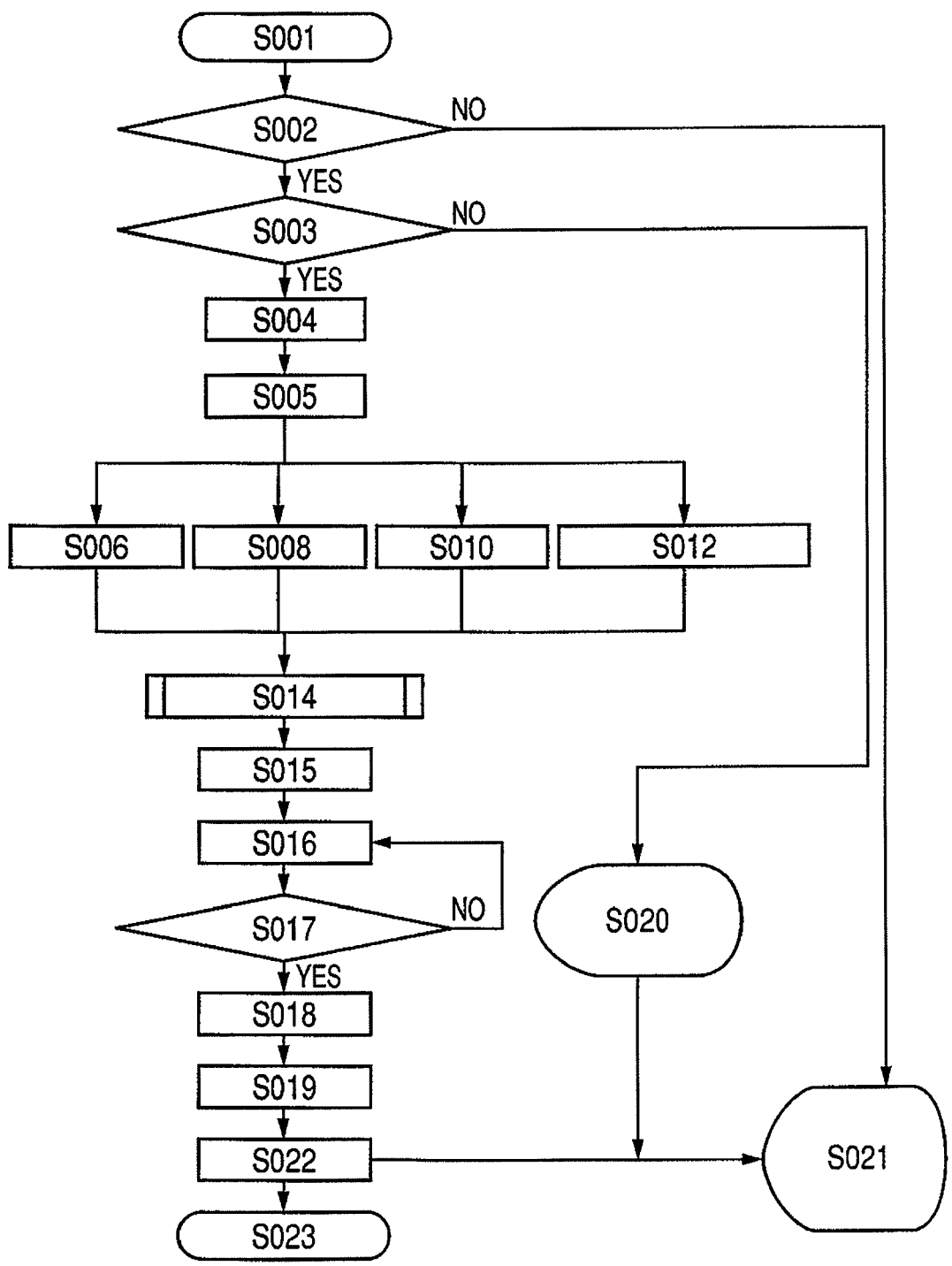
FIG. 5 is a flow chart showing an example of an inhalation process using the medicine ejection device of the present invention.

In the following, an inhalation process according to this embodiment is described with reference to a flow chart shown in FIG. 5.

First, when a power switch is pushed by a user, the device is brought into the starting mode (S001: START). After the starting mode has been activated, it is checked whether or not the medicine ejection unit 6 is loaded (S002: EJECTION UNIT ON?). If it is not loaded, a warning to inform the user of the fact that the medicine ejection unit 6 is not loaded is displayed (S021: WARNING, REPLACE EJECTION UNIT), and power supply is shut off (S022: POWER OFF), through which the device is stopped (S023: END).

Where, e.g., the medicine ejection unit 6 is provided with a liquid ejection head having an ejection energy generating means in a thermal jet system, a detecting means of the medicine ejection unit 6 is aimed at measuring the resistance value of a heater serving as the ejection energy generating means.

Where the medicine ejection unit 6 is loaded, the remaining power of the battery is checked (S003: BATTERY REMAINING POWER OK?). If it is running short, a direction to replace or charge the battery is displayed (S020: WARNING, REPLACE BATTERY), and power supply is shut off (S022: POWER OFF), through which the device is stopped (S023: END).

Where the remaining power of the battery has been judged to be enough for performing inhalation operation at least once, the power is switched on (S004: POWER ON), and initialization is carried out (S005: INITIALIZATION). This initialization is to set a standard ejection operating period for which the total amount of liquid droplets to be ejected is achievable corresponding to the dose according to prescription concerned with each individual user.

After the initialization has been completed (S005: INITIALIZATION), any one of the medicine temperature, open-air temperature, open-air humidity and open-air atmospheric pressure is selected, and its correction factor is decided on the basis of a measured value found by using the measuring means selected. According to the value found when the standard ejection operating period is multiplied by the correction factor thus decided, the standard ejection operating period is corrected to decide the ejection operating period.

Figure 7:
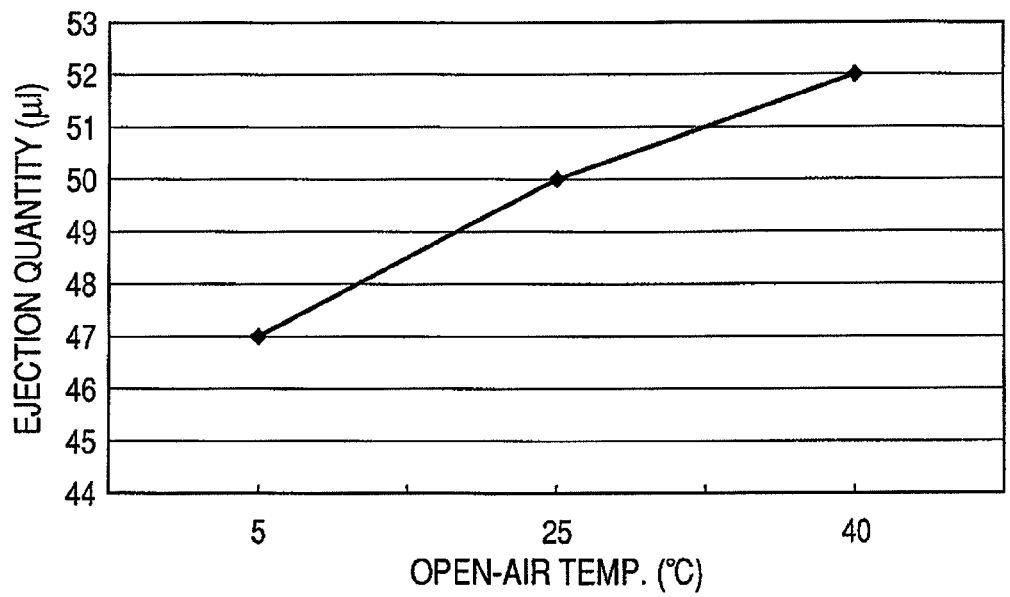
FIG. 7 is a graph showing the relationship between open-air temperature and ejection quantity in the medicine ejection device of the present invention.

In the step of measuring open-air temperature, the open-air temperature is measured with the temperature-humidity sensor 12 provided on the control motherboard 11 (S006: OPEN-AIR TEMPERATURE MEASUREMENT), and the correction factor to correct fluctuations of ejection quantity which are caused by the open-air temperature is decided (S014: CORRECTION FACTOR DECISION). That is, an open-air temperature correction factor is decided by using the CPU, RAM and ROM provided on the control motherboard 11 of the inhaler. The relationship between open-air temperature and ejection quantity is shown in FIG. 7. Using an ejection head of 3 μm in nozzle diameter, a medicine was ejected in an environment having an open-air relative humidity of 50%, an atmospheric pressure of 1,013 hPa and a medicine temperature of 25° C. The composition of the medicine ejected is shown in Table 5. As shown in FIG. 7, the open-air temperature and the ejection quantity have a substantially linear relation, where the ejection quantity increases with a rise in open-air temperature and the ejection quantity decreases with a fall in open-air temperature. Accordingly, when the open-air temperature is higher, the ejection operating period is so corrected as to be shortened and, when the open-air temperature is lower, the ejection operating period is so corrected as to be elongated according to the correction factor. Where a standard is set to be an ejection operating period for which the medicine is to be ejected in a quantity corresponding to the dose of the medicine when the open-air temperature is 25° C., it follows that correction factors can be decided as shown in Table 1.

Figure 8:
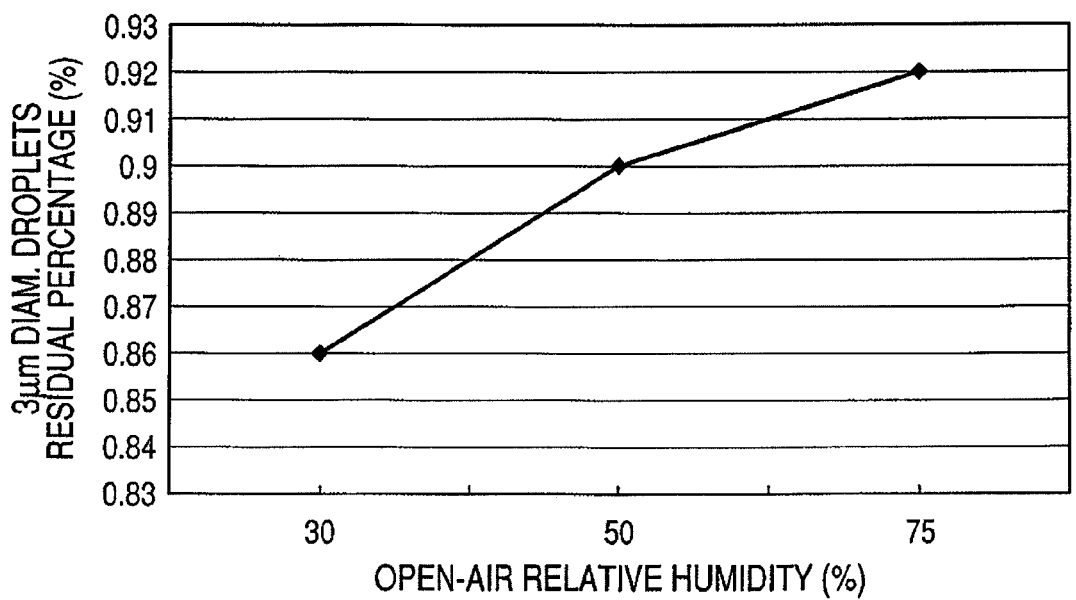
FIG. 8 is a graph showing the relationship between open-air humidity and residual percentage in the medicine ejection device of the present invention where the residual percentage is a percentage of liquid droplets of 3 μm in droplet diameter among liquid droplets having been ejected.

In the step of measuring open-air humidity, the open-air humidity is measured with the temperature-humidity sensor 12 provided on the control motherboard 11 (S008: OPEN-AIR HUMIDITY MEASUREMENT), and an open-air humidity correction factor is decided by using the CPU, RAM and ROM (S014: CORRECTION FACTOR DECISION). The relationship between open-air humidity and changes in droplet diameter is shown in FIG. 8. Using an ejection head having a nozzle diameter of 3 μm, a medicine was ejected in an environment having an open-air temperature of 25° C., an atmospheric pressure of 1,013 hPa and a medicine temperature of 25° C. The composition of the medicine ejected is shown in Table 5. As shown in FIG. 8, with a decrease in humidity, the proportion of liquid droplets having a droplet diameter of 3 μm decreases in relation to respect to a lapse of time, so that the medicine that can reach the desired portion is reduced. Accordingly, with an increase in humidity, correction is so made that the correction factor becomes smaller. Where a relative humidity of 50% is set to be a standard, any correction factor may be decided as shown in Table 2.

In the step of measuring open-air atmospheric pressure, the open-air atmospheric pressure is measured with the pressure sensor 13 provided on the control motherboard 11 (S010: OPEN-AIR ATMOSPHERIC-PRESSURE MEASUREMENT).

Figure 9:
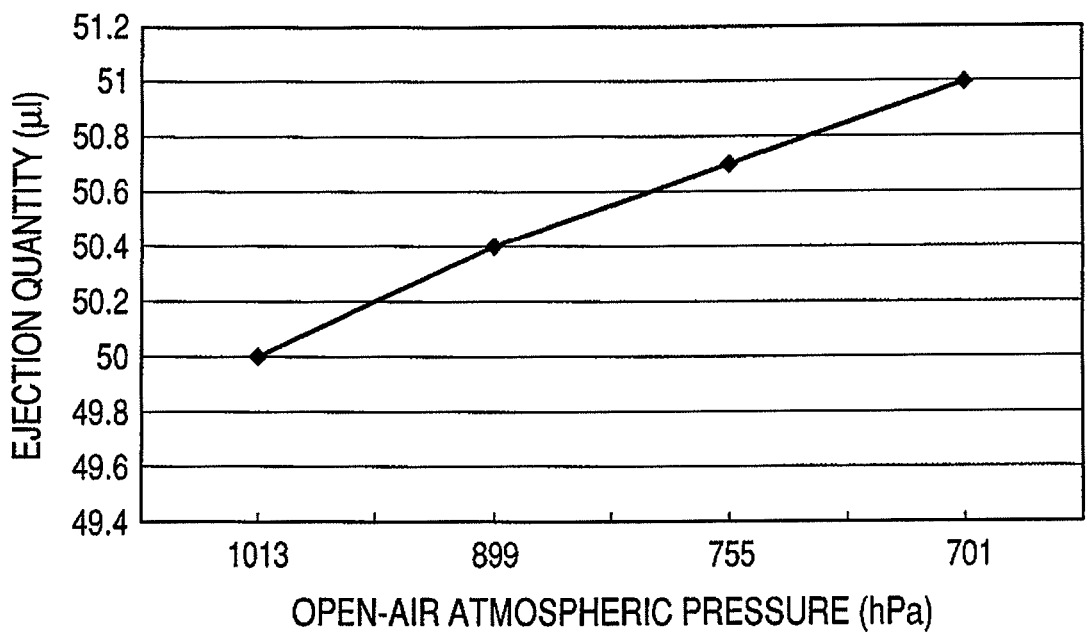
FIG. 9 is a graph showing the relationship between open-air atmospheric pressure and ejection quantity in the medicine ejection device of the present invention.

The pressure sensor 13 may be of, e.g., a resistance change type in which changes in pressure are converted into resistance values, an electrostatic capacity type in which changes in pressure are converted into changes in the quantity of static electricity and a quartz oscillation frequency type in which changes in pressure are converted into oscillation frequencies. On the basis of the open-air atmospheric pressure measured with this pressure sensor 13, an open-air atmospheric pressure correction factor is decided by using the CPU, RAM and ROM (S014: CORRECTION FACTOR DECISION). The relationship between open-air atmospheric pressure and ejection quantity is shown in FIG. 9. Using an ejection head having a nozzle diameter of 3 μm, a medicine was ejected in an environment having an open-air relative humidity of 50%, an open-air temperature of 25° C. and a medicine temperature of 25° C. The composition of the medicine ejected is shown in Table 5. As shown in FIG. 9, the ejection quantity tends to increase with a decrease in open-air atmospheric pressure. Accordingly, it follows that correction is so made that the correction factor is made smaller with a decrease in atmospheric pressure. Where 1 atmospheric pressure (1 atm; 1,013 hPa) is set to be a standard, any correction factor may be decided as shown in Table 3.

Figure 10:
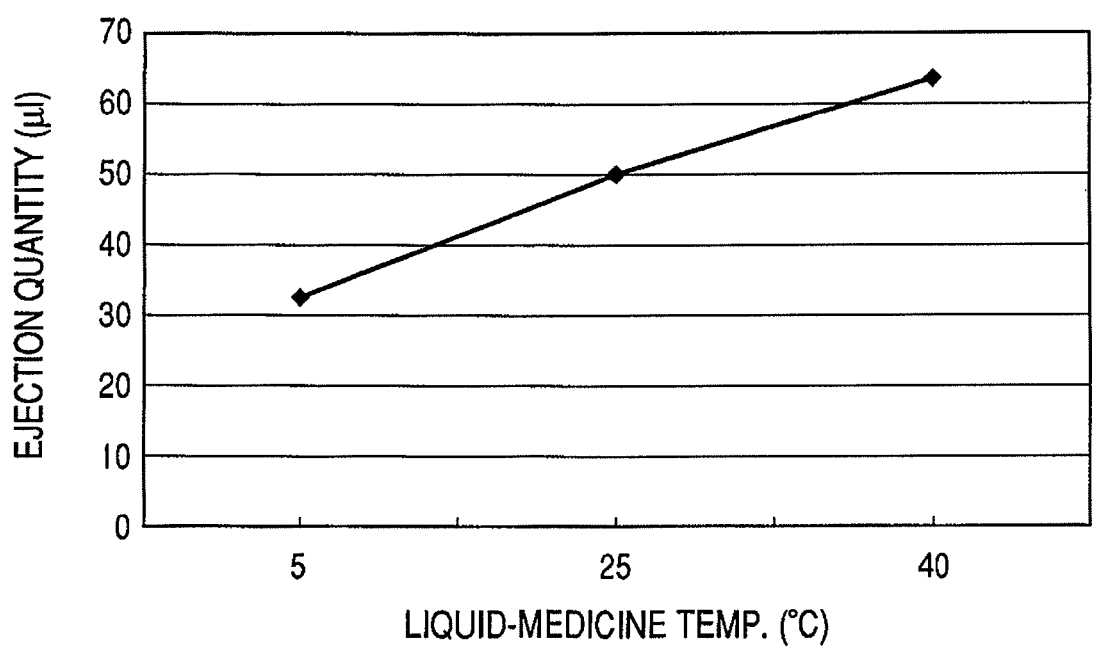
FIG. 10 is a graph showing the relationship between liquid-medicine temperature and ejection quantity in the medicine ejection device of the present invention.

In the step of measuring medicine temperature, the temperature of the medicine tank 7 is measured with the temperature sensor 17 provided on the control motherboard 11 (S012: MEDICINE TANK TEMPERATURE MEASUREMENT). Then, on the basis of the medicine temperature thus measured, a medicine temperature correction factor is decided by using the CPU, RAM, ROM and so forth provided on the control motherboard 11 (S014: CORRECTION FACTOR DECISION). The relationship between medicine temperature and ejection quantity is shown in FIG. 10. Using an ejection head having a nozzle diameter of 3 μm, a medicine was ejected in an environment having an open-air relative humidity of 50%, an open-air temperature of 25° C. and an atmospheric pressure of 1,013 hPa. The composition of the medicine ejected is shown in Table 5. As shown in FIG. 10, the medicine temperature and the ejection quantity have a substantially linear relation, where the ejection quantity increases with a rise in medicine temperature and the ejection quantity decreases with a fall in medicine temperature. Accordingly, it follows that correction is so made that the correction factor is made smaller with an increase in medicine temperature. Where a medicine temperature of 25° C. is set to be a standard, any correction factor may be decided as shown in Table 4. The temperature sensor 17 to be used may be of a radiation type in non-contact with the medicine tank 7, or a surface temperature sensor type which uses a thermocouple.

Any one of the above open-air temperature correction factor, open-air humidity correction factor, open-air atmospheric-pressure correction factor and medicine temperature correction factor is selected to decide the correction factor (S014: CORRECTION FACTOR DECISION). Then, according to the value found when the standard ejection operating period is multiplied by the correction factor thus selected, the standard ejection operating period is corrected to decide the ejection operating period (S015: EJECTION OPERATING PERIOD DECISION), and inhalation is ready to be started (S016: READY).

As for the order of priority of selecting any one of the use conditions, i.e., open-air temperature, open-air humidity, open-air atmospheric pressure and medicine temperature, it is preferable to sequentially select one of them which has a larger influences than the others on the ejection quantity of liquid droplets of the medicine more greatly, e.g., in the order of (1) the medicine temperature, (2) the open-air temperature, (3) the open-air humidity and (4) the open-air atmospheric pressure. For example, where the medicine temperature is measured to decide its correction factor, it is sufficient that in FIGS. 4A and 4B, the temperature sensor 17 is provided, and the temperature-humidity sensor 12 and the pressure sensor 13 need not be provided. The same is applied to the cases where other conditions are measured. For example, assuming that the medicine has just taken out of a refrigerator in an environment of 25° C. and the medicine temperature is 5° C., and where the standard ejection operating period is set to be 1.1 seconds, the ejection operating period is 1.1×1.563=1.7193.

Upon detection of the inhalation (S017: INHALATION ON), ejection operation is started at a certain frequency (S018: UNDER INHALATION). At this stage, the device may notify the user that the device is under inhalation, through display, vibration from a vibrating motor or sound. Thereafter, the ejection operating period elapses and ejection pulse signals are stopped from being fed, thus the ejection operation is completed (S019: EJECTION OPERATION COMPLETED). Upon completion of the ejection operation, power supply is shut off (S022: POWER OFF), through which the device is stopped (S023: END).

The method of deciding the corrected ejection operating period is by no means limited to the method in which the standard ejection operating period is multiplied by the correction factor. For example, a table of corrected ejection operating period values may be stored in the RAM, where a corresponding corrected ejection operating period value is directly read for each measured value, and each ejection operating period may be decided on the basis of each corrected ejection operating period value.

EXAMPLE 2

Figure 6:
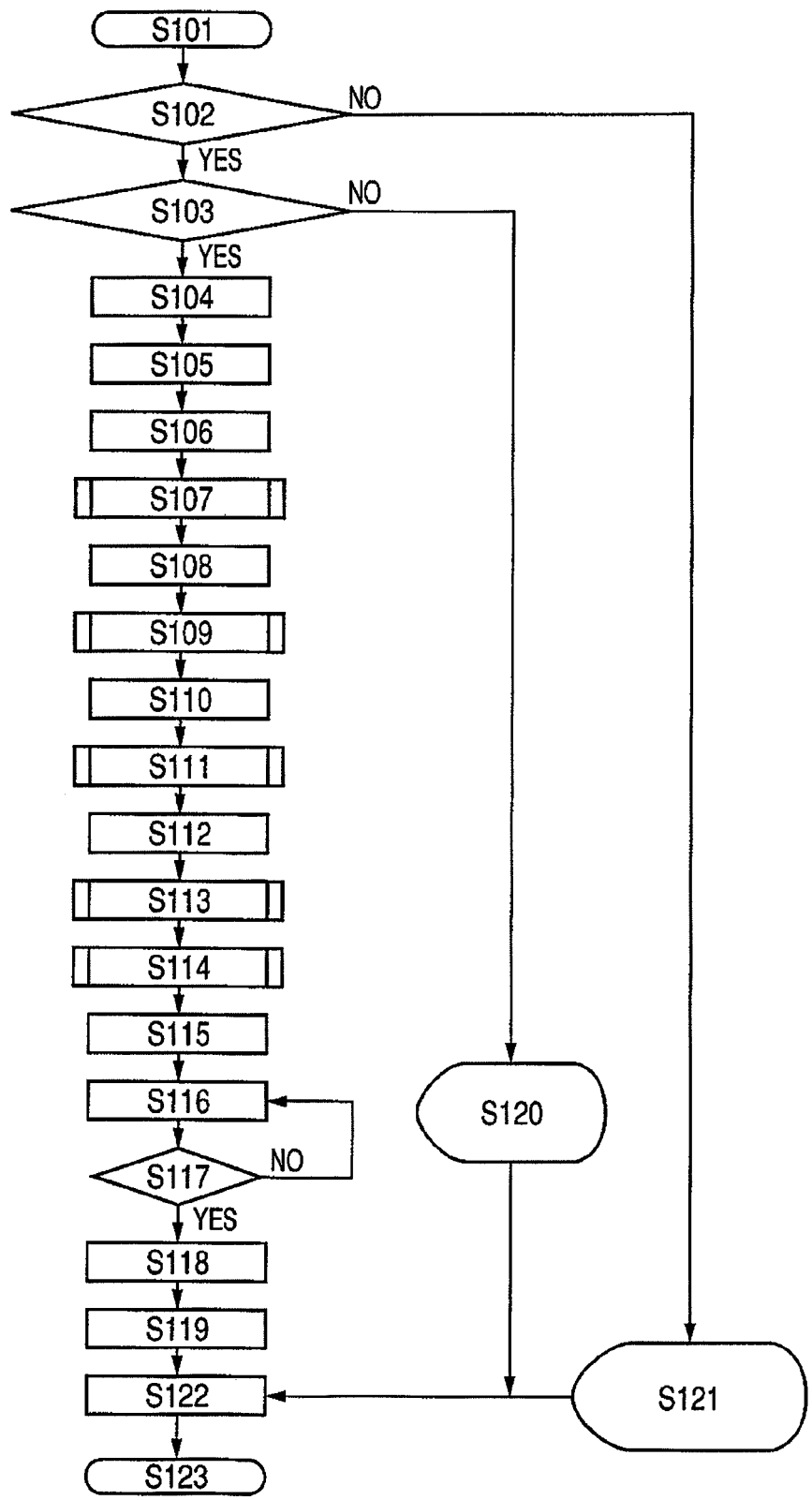
FIG. 6 is a flow chart showing another example of an inhalation process using the medicine ejection device of the present invention.

An inhalation process according to another embodiment will be described along the flow chart shown in FIG. 6. In this embodiment, all the above parameters are measured and taken into account to decide the ejection operating period.

First, when a power switch is pushed by a user, the device is brought into the starting mode (S101: START). After the starting mode has been activated, it is checked whether or not the medicine ejection unit 6 is loaded (S102: EJECTION UNIT ON?). If it is not loaded, a warning to inform the user of the fact that the medicine ejection unit 6 is not loaded is displayed (S121: WARNING, REPLACE EJECTION UNIT), and power supply is shut off (S122: POWER OFF), through which the device is stopped (S123: END).

Where, e.g., the medicine ejection unit 6 effects ejection by an ejection head 8 having an electrothermal conversion element in a thermal jet system, a detecting means of the medicine ejection unit 6 is aimed at measuring the resistance value of the element.

Where the medicine ejection unit 6 is loaded, the remaining power of the battery is checked (S103: BATTERY REMAINING POWER OK?). If it is running short, a direction to replace or charge the battery is displayed (S120: WARNING, PLS REPLACE BATTERY), and power supply is shut off (S122: POWER OFF), through which the device is stopped (S123: END).

Where the remaining power of the battery has been judged to be enough for performing inhalation operation at least once, the power is switched on (S104: POWER ON), and initialization is carried out (S105: INITIALIZATION). This initialization is to set a standard ejection operating period for which the total amount of liquid droplets to be ejected is achievable corresponding to the dose according to prescription concerned with each individual user.

After the initialization has been completed (S105: INITIALIZATION), the open-air temperature is measured with the temperature-humidity sensor 12 provided on the control motherboard 11 (S106: OPEN-AIR TEMPERATURE MEASUREMENT), and an open-air temperature correction factor is decided by using the CPU, RAM and ROM provided on the control motherboard 11 (S107: OPEN-AIR TEMPERATURE CORRECTION FACTOR DECISION).

Next, in the step of the measuring open-air humidity, the open-air humidity is measured with the temperature-humidity sensor 12 provided on the control motherboard 11 (S108: OPEN-AIR HUMIDITY MEASUREMENT), and an open-air humidity correction factor is decided by using the CPU, RAM and ROM (S109: OPEN-AIR HUMIDITY CORRECTION FACTOR DECISION) in the same way as in the open-air temperature correction factor.

Next, in the step of measuring open-air atmospheric pressure, the open-air atmospheric pressure is measured with the pressure sensor 13 provided on the control motherboard 11 (S110: OPEN-AIR ATMOSPHERIC-PRESSURE MEASUREMENT). The pressure sensor 13 may be of, e.g., a resistance change type in which changes in pressure are converted into resistance values, an electrostatic capacity type in which changes in pressure are converted into changes in quantity of static electricity and a quartz oscillation frequency type in which changes in pressure are converted into oscillation frequencies. On the basis of the open-air atmospheric pressure measured with this pressure sensor 13, an open-air atmospheric pressure correction factor is decided by using the CPU, RAM, ROM and so forth provided on the control motherboard 11 (S111: OPEN-AIR ATMOSPHERIC-PRESSURE CORRECTION FACTOR DECISION).

Finally, in the step of measuring medicine temperature, the temperature of the medicine tank 7 is measured with the temperature sensor 17 provided on the control motherboard 11 (S112: MEDICINE TANK TEMPERATURE MEASUREMENT). Then, on the basis of the medicine temperature thus measured, a medicine temperature correction factor is decided by using the CPU, RAM and ROM provided on the control motherboard 11 (S113: MEDICINE TEMPERATURE CORRECTION FACTOR DECISION). The temperature sensor 17 to be used may be of a radiation type in non-contact with the medicine tank 7 or a surface temperature sensor type which uses a thermocouple.

The above open-air temperature correction factor, open-air humidity correction factor, open-air atmospheric pressure correction factor and medicine temperature correction factor are used to decide a total correction factor (S114: TOTAL CORRECTION FACTOR DECISION). Then, according to a corrected ejection operating period which is the value found when the standard ejection operating period is multiplied by the total correction factor, the standard ejection operating period is corrected to decide the ejection operating period (S115: EJECTION OPERATING PERIOD DECISION), and inhalation is ready to be started (S116: READY). The standard ejection operating period is set to be a time necessary for ejecting the medicine in a quantity corresponding to the dose of the medicine when ejected under the condition set as a standard in determining the correction factor of each parameter in Example 1. In the following description, the same example as in Example 1 will be taken. In the case where the open-air temperature is 25° C., the open-air relative humidity is 50%, the open-air atmospheric pressure is 1,013 hPa, and the medicine temperature is 25° C., the ejection operating period is set to be 1.1 seconds (standard ejection operating period). Assuming that the open-air temperature is 40° C., the open-air humidity is 75%, the open-air atmospheric pressure is 701 hPa upon inhalation at a highland of 3,000 m in altitude and the medicine temperature is 5° C., the ejection operating period is as follows:

(1.563×0.962×0.978×0.980)×1.1=1.585 seconds.

Upon detection of the inhalation (S117: INHALATION ON), ejection operation is started using a certain frequency (S118: UNDER INHALATION). At this stage, the device may notify the user that the device is under inhalation, through display, vibration from a vibrating motor or sound. The device may have such a means. Thereafter, the ejection operating period corrected elapses and ejection pulse signals are stopped from being fed, thus the ejection operation is completed (S119: EJECTION OPERATION COMPLETED). Upon completion of the ejection operation, power supply is shut off (S122: POWER OFF), through which the device is stopped (S123: END).

In order to make a more accurate correction, it is preferable to measure all the four conditions (open-air temperature, open-air humidity, open-air atmospheric pressure and medicine temperature). However, the inhaler according to the above Example 2 may be so modified that two or three among the four measurements are selected and the total correction factor of the two or three conditions selected is decided. With such a modification, an inhalation process can be carried out following the inhalation process indicated in the flow chart shown in the FIG. 6 in the above Example 2. Accordingly, description therefor is omitted. In this case, when, e.g., any three conditions other than the open-air atmospheric pressure are measured to decide the ejection operating period on the basis of their total correction factors, the pressure sensor 13 shown in FIG. 4A need not be provided.

In the present invention, each correction factor is affected by the content of the medicine, and hence, is a numerical value that may change depending on the type of medicine.

It is also possible to decide the ejection operating period as follows: a table of corrected ejection operating period values may be stored in the RAM, where a corresponding corrected ejection operating period value is directly read for each measured value in each open-air environment, and each ejection operating period may be decided on the basis of each corrected ejection operating period value.

The present invention may be used for various purposes besides use for medicine inhalation. For example, it may be used for various purposes where require sure and sanitary ejection of liquid droplets, for example, as an inhaler for fragrances, or an inhaler for luxury items such as nicotine.

TABLE 1

Open-Air Temperature/Ejection Correction Factor

| | Open-air temperature (° C.) | | |
|---|---|---|---|
| | 5 | 25 | 40 |
| Ejection Correction Factor | 1.064 | 1 | 0.962 |

TABLE 2

Open-Air Humidity/Ejection Correction Factor

| | Open-air relative humidity (%) | | |
|---|---|---|---|
| | 30 | 50 | 75 |
| Ejection Correction Factor | 1.046 | 1 | 0.978 |

TABLE 3

Open-Air Atm. Pressure/Ejection Correction Factor

| | Open-air atmospheric pressure (hPa) | | | |
|---|---|---|---|---|
| | 1013 | 899 | 755 | 701 |
| Ejection Correction Factor | 1 | 0.992 | 0.986 | 0.980 |

TABLE 4

Medicine Temperature/Ejection Correction Factor

| | Medicine temperature (° C.) | | |
|---|---|---|---|
| | 5 | 25 | 40 |
| Ejection Correction Factor | 1.563 | 1 | 0.790 |

TABLE 5

| Components | Action | Concentration |
|---|---|---|
| Ipratorium bromide | Anticholinergic | 0.3 mg/mL |
| Fenoterol hydrobromide | $\beta_2$ stimulant | 1.3 mg/mL |
| Benzalkonium chloride | Antibacterial | 0.1 mg/mL |
| Sodium edetate | Stabilizer | 0.5 mg/mL |

The present invention is not limited to the above embodiments and various changes and modifications can be made within the spirit and scope of the present invention. Therefore, to apprise the public of the scope of the present invention, the following claims are made.

This application claims the benefit of Japanese Patent Application Nos. 2006-201432, filed Jul. 25, 2006, and 2007-177023, filed Jul. 5, 2007, which are hereby incorporated by reference herein in their entirety.

What is claimed is:

1. A medicine ejection device for ejecting a medicine to be administered to a user, the device comprising:
   a medicine temperature measuring sensor for measuring the temperature of the medicine, a temperature sensor for measuring the temperature of the open air, a humidity sensor for measuring the humidity of the open air and an atmospheric-pressure sensor for measuring the atmospheric pressure of the open air; and
   a decision part for deciding ejection operating conditions of a medicine ejection part comprising an ejection head for ejecting the medicine, in accordance with the temperature of the medicine, the temperature of the open air, the humidity of the open air and the atmospheric pressure of the open air during use of the device,
   wherein the device is configured to eject the medicine from the ejection head according to the ejection operating conditions decided by the decision part, and
   wherein the medicine ejection device is so constituted as to conduct measurement with the medicine temperature measuring sensor after measurement with the temperature sensor, the humidity sensor and the atmospheric-pressure sensor.

2. The medicine ejection device according to claim 1, wherein the decision part is configured to decide an ejection operating period for which the medicine is to be ejected from the ejection head in a quantity corresponding to the dose of the medicine.

3. A medicine ejection device according to claim 1, the device further comprising:
   a medicine holding part for holding the medicine; and
   the medicine ejection part comprising the ejection head for ejecting the medicine fed from the medicine holding part according to the ejection operating conditions decided by the decision part.

4. The medicine ejection device according to claim 3, wherein the medicine ejection part has an electrothermal conversion element for providing the medicine with thermal energy or an electromechanical conversion element for providing the medicine with mechanical energy.

* * * * *